United States Patent
Block et al.

(10) Patent No.: US 6,596,768 B2
(45) Date of Patent: Jul. 22, 2003

(54) UNSATURATED LIPID-ENRICHED FEEDSTOCK FOR RUMINANTS

(75) Inventors: Elliot Block, Yardley, PA (US); William K. Sanchez, Tigard, OR (US); Kenneth R. Cummings, Skillman, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 09/863,540

(22) Filed: May 22, 2001

(65) Prior Publication Data

US 2003/0007998 A1 Jan. 9, 2003

(51) Int. Cl.$^7$ .......................... A61K 31/20; A61K 31/35
(52) U.S. Cl. ........................................ 514/560; 514/460
(58) Field of Search ................................. 514/560, 460

(56) References Cited

U.S. PATENT DOCUMENTS

| | | | |
|---|---|---|---|
| 3,839,557 A | 10/1974 | Raun | 424/115 |
| 4,642,317 A | 2/1987 | Palmquist et al. | 514/558 |
| 4,909,138 A | 3/1990 | McAskie | 99/536 |
| 5,380,893 A * | 1/1995 | Lajoie | 554/156 |
| 5,391,788 A | 2/1995 | Vinci et al. | 514/156 |
| 5,456,927 A | 10/1995 | Vinci et al. | 426/74 |
| 5,547,686 A | 8/1996 | Jenkins | 426/2 |
| 5,874,102 A | 2/1999 | LaJoie et al. | 424/438 |

OTHER PUBLICATIONS

T.S. Rumsey, "Monensin in Cattle: Introduction", 1984, Journal of Animal Science, vol. 58, No. 6, pp. 1461–1483.

R. D. Goodrich et al., "Influence of Monensin on Monensin on the Performance of Cattle", 1984, Journal of Animal Science, vol. 58, No. 6, pp. 1484–1498.

Gerald T. Schelling, "Monensin Mode of Action in the Rumen", 1984, Journal of Animal Science, vol. 58, No. 6, pp. 1518–1527.

James B. Russell et al., "Effect Of Ionophores On Ruminal Fermentation", Jan. 1989, Applied and Environmental Microbiology, pp. 1–6.

C. Van Nevel et al., "Lipolysis and Biohydrogenation of Soybean Oil in the Rumen In Vitro: Inhibition by Antimicrobials", 1995, Journal of Dairy Science, vol. 78, No. 12, pp. 2797–2806.

V. Fellner et al., "Effect of Nigericin, Monensin, and Tetronasin on Biohydrogenation in Continuous Flow–Through Ruminal Fermenters", 1997, Journal of Dairy Science, vol. 80, No. 5, pp. 921–928.

* cited by examiner

*Primary Examiner*—Kevin E. Weddington
(74) *Attorney, Agent, or Firm*—Stephen B. Shear

(57) ABSTRACT

This invention provides a feedstock for ruminants which beneficially improves feed efficiency and body growth. The feedstock also is adapted to improve the lactational performance of dairy cattle. The recovered milk product has a milk fat profile with an increased proportion of unsaturated fatty acid constituents. The enhanced benefits exhibited by an invention feedstock are derived from essential ingredients such as unsaturated fatty acid derivative having rumen-bypass properties, and an effective additive quantity of cyclic polyether ionophorous antibiotic.

12 Claims, No Drawings

UNSATURATED LIPID-ENRICHED FEEDSTOCK FOR RUMINANTS

BACKGROUND OF THE INVENTION

This invention generally relates to feedstock for domesticated ruminants. More specifically this invention relates to an unsaturated lipid supplemented feedstock for ruminants which beneficially provides an increased production of propionate in the rumen and a resultant improved feed efficiency and body growth in the ruminant.

Conventional cattle feeds such as corn and alfalfa often fail to provide sufficient energy for cattle, especially lactating dairy cattle during periods of heavy milk production. Feed containing a high proportion of corn also has a tendency to depress the milk fat content of the milk produced by such cattle. Lipid is an excellent energy source, and it is known that if the proportion of lipid in cattle food is increased, lactating dairy cattle produce high milk yields without draining their reserves of body fat and without diminishing the proportion of milk fat in the milk produced.

However, it has been found that if the proportion of lipid in the diet of cattle exceeds about 3–5% of the total feed solids, the feed has toxic effects upon the microorganisms in the rumen of the cattle. It appears that lipid reduces the growth rate or even kills certain microorganisms which digest fiber in the cow's rumen, thereby lowering fiber digestibility. This deleterious effect on the cow's rumen is particularly true of unsaturated lipids. Although the decreased fiber digestion in the rumen is partially compensated by greater fiber digestion in the lower parts of the alimentary canal, such later fiber digestion produces a blend of different fatty acids than that which is produced by the digestion in the rumen, and the different blend of fatty acids is less suited to the cow's metabolism.

U.S. Pat. Nos. 4,642,317; 4,826,694; 4,853,233; and 4,909,138 describe the incorporation of insoluble fatty acid salts in ruminant feed as a means of increasing the fat content of the feed without deleteriously affecting the ruminant digestion cycle. A feed additive such as fatty acid calcium salt functions as a rumen-bypass product, and is subsequently metabolized in the abomasum or small intestine of the ruminant.

Many dietary lipids contain a large proportion of unsaturated fatty acids. Under the usual feeding conditions for lactating cattle, however, these unsaturated fatty acids do not appear in cow milk because they are extensively biohydrogenated to more saturated fatty acids (e.g., stearic acid) by the ruminal microbial population.

Of related interest with respect to the present invention are publications that describe studies of factors which influence biohydrogenation of unsaturated fatty acids under ruminal conditions.

J. Dairy Sci., 78, 2797 (1995) reports in vitro experiments directed to the antimicrobial inhibition of lipolysis and lipid biohydrogenation of soybean oil in rumen fluid. The most potent inhibitors are ionophores and amoxicillin.

An "ionophore" is illustrated by monensin which is a cyclic polyether antibiotic that is naturally by occurring in *Streptomyces cinnamonensis*.

Ionophores have been utilized extensively in the diets of ruminants, and effects on animal performance are well documented. Improved animal performance in part derives from the ability of ionophores to alter ruminal fermentation. Dietary ionophores increase the ratio of propionate to acetate, and inhibit ruminal methanogenesis. Changes in ruminal fermentation pathways are attributed to the disruptive action of ionophores on the permeability of ions across bacterial membranes. Different ionophores vary in their affinity and binding selectivity for cations.

There is limited information on the effect of ionophores on ruminal lipid metabolism. Dietary unsaturated fatty acids are extensively biohydrogenated by ruminal bacteria, a process that requires energy for reduction and can serve as means for disposal of hydrogen. It has been suggested that ionophores reduce methane production by inhibiting the growth of Gram-positive bacteria that produce hydrogen, and thereby decrease ruminal biohydrogenation of unsaturated fatty acids. Limited studies have indicated that dietary ionophores alter lipid metabolism in the rumen, with a resulting increase of unsaturated fatty acids in ruminal bacteria and in the duodenal digesta.

There is continuing interest in developments relating to improved materials and procedures for advancing ruminant husbandry, and for providing value-added meat and dairy products for human consumption.

Accordingly, it is an object of this invention to provide a ruminant feedstock which yields improved feed efficiency and body growth in ruminants.

It is another object of this invention to provide an unsaturated lipid supplement for ruminant feedstock with lipids that exhibit rumen-bypass properties, and which has a content of ionophorous antibiotic additive.

It is another object of this invention to provide a method for improving the lactational performance of ruminants.

It is a further object of this invention to provide a cow milk product which has a milk fat profile with an increased molar proportion of unsaturated fatty acid constituents.

Other objects and advantages of the present invention shall become apparent from the accompanying description and example.

DESCRIPTION OF THE INVENTION

One or more objects of the present invention are accomplished by the provision of a feedstock adapted for beneficial feeding to a ruminant, which feedstock comprises (1) nutritionally balanced ration; (2) between about 2–20 weight percent, on a dry weight basis, of lipid ingredient comprising unsaturated fatty acid derivative having rumen-bypass properties; and (3) an effective quantity of cyclic polyether ionophorous antibiotic ingredient; wherein a ruminant feeding regimen with the feedstock induces an increased production of propionate in the rumen, and a resultant improved feed efficiency and body growth in the ruminant.

A typical feedstock for ruminants such as lactating cattle will include silage, and energy concentrate and protein concentrate. A basal feedstock can comprise (6.4) corn silage (35% dry matter), (17) alfalfa silage (50% dry matter), (1) alfalfa hay, and (6.9) energy and (2.1) protein concentrate.

The compositions of an energy concentrate and a protein concentrate are illustrated in TABLE 1.

TABLE 1

| | Weight, % |
|---|---|
| ENERGY CONCENTRATE | |
| Ground shelled corn | 56.87 |
| Ground ear corn | 34.50 |
| Molasses | 2.00 |
| Animal/vegetable fat | 1.00 |
| Minerals and vitamins | 5.63 |

TABLE 1-continued

|  | Weight, % |
| --- | --- |
| PROTEIN CONCENTRATE | |
| Soybean meal - 44% | 60.88 |
| Soybran hulls | 26.20 |
| Molasses | 1.00 |
| Fish meal | 3.90 |
| Animal/vegetable fat | 1.00 |
| Sodium bicarbonate | 3.90 |
| Magnesium oxide | 0.92 |

One or more other ingredients can be incorporated in a present invention feedstock composition, such as biologically active derivatives.

An optional biologically active ingredient can be included in a feedstock in an effective quantity between about 0.05–20 weight percent, based on the weight of feedstock. It can be selected from a broad variety of nutrients and medicaments, either as a single component or as a mixture of components, which are illustrated by the following listing of active species:

1. sugars and complex carbohydrates which include both water-soluble and water-insoluble monosaccharides, disaccharides and polysaccharides.

Cane molasses is a byproduct from the extraction of sucrose from sugar cane. It is commercially available at standard 79.5° Brix concentration, which has a water content of about 21 weight percent, and a sugar content of 50 weight percent. Sugar beet byproducts also are available as low cost carbohydrate sources.

Whey is a byproduct of the dairy industry. The whey is a dilute solution of lactalbumin, lactose, fats, and the soluble inorganics from milk. Dried whey solids typically have the following composition:

|  |  |
| --- | --- |
| Protein | 12.0% |
| Fat | 0.7% |
| Lactose | 60.0% |
| Phosphorus | 0.79% |
| Calcium | 0.874% |
| Ash | 9.7% |

Another source of carbohydrate is derived from the pulp and paper industry which produces large quantities of byproduct lignin sulfonates from wood during the sulfite pulping process. The carbohydrate byproduct is a constituent of the spent sulfite liquor.

2. aminoacid ingredients either singly or in combination which include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cysteine ethyl HCl, and the like, and analogs and salts thereof.

3. vitamin ingredients either singly or in combination which include thiamine HCl, riboflavin, pyridoxine HCl, niacin, niacinamide, inositol, choline chloride, calcium pantothenate, biotin, folic acid, ascorbic acid, vitamin $B_{12}$, p-aminobenzoic acid, vitamin A acetate, vitamin K, vitamin D, vitamin E, and the like.

Trace element ingredients include compounds of cobalt, copper, manganese, iron, zinc, tin, nickel, chromium, molybdenum, iodine, silicon, vanadium and selenium.

4. protein ingredients as obtained from sources such as dried blood or meat meal, dried and sterilized animal and poultry manure, fish meal, liquid or powdered egg, fish solubles, cell cream, soybean meal, cottonseed meal, canola meal, and the like.

Protein ingredients include non-protein nitrogen compounds such as urea, biuret, ammonium phosphate, and the like.

5. antioxidants as illustrated by butylated hydroxyanisole, butylated hydroxytoluene, tocopherol, tertiary-butylhydroquinone, propyl gallate, and ethoxyquin; and suitable preservatives include sodium sorbate, potassium sorbate, sodium benzoate, propionic acid, α-hydroxybutyric acid, and the like.

6. suspension stabilizing agents which preferably are selected from nonionic surfactants, hydrocolloids and cellulose ethers. These types of chemical agents are illustrated by polyethylene oxide condensates of phenols, C8–C22 alcohols and amines; ethylene oxide reaction products with fatty acid partial esters of hexitans; alkylarylpolyoxyethylene glycol phosphate esters; gum arabic; carob bean gum; tragacanth gum; ammonium, sodium, potassium and calcium alginates; glycol alginates; xanthan gum; potato agar; alkylcellulose; hydroxyalkylcellulose; carboxyalkylcellulose; and the like.

The feedstock initially is metabolized in the rumen of cattle and other ruminants. The rumen contains microorganisms, such as bacteria and protozoa, which break down complex compounds ingested by the animal via a fermentation process.

The essential lipid ingredient of an invention feedstock comprises unsaturated fatty acid derivative having rumen-bypass properties. The lipid derivative can be in the form of fatty acid alkaline earth metal salt, such as calcium and/or magnesium salt. The lipid derivative also can be in the form of fatty acid amide, in which the amide nitrogen is substituted with hydrogen and/or aliphatic radicals. Fatty acid salts and amides having rumen-bypass properties are described in publications such as U.S. Pat. Nos. 4,642,317; 4,826,694; 5,391,788; 5,425,693; 5,456,927; 5,496,572, 5,547,686; 5,670,191; 5,874,102; and the like, incorporated by reference.

A preferred group of unsaturated fatty acids are 18-carbon structures such as oleic acid, linoleic acid, conjugated linoleic acid, linolenic acid, alpha-linolenic acid, and the like. Also preferred are unsaturated fatty acids such as eicosapentaenoic acid, docosapentaenoic acid, tetracosapentaenoic acid, docosahexaenoic acid, and the like.

A normal feeding regimen can provide between about 300–1200 grams per day of lipid ingredient to a ruminant such as a lactating dairy cow.

The essential ionophorous antibiotic ingredient of an invention feedstock is added in a quantity which is effective for improving the health and productivity of ruminants. The content of the ionophorous antibiotic in the feedstock typically will be in the range between about 5–80 milligrams per kilogram DM of feedstock. For feeding lactating dairy cattle, a convenient measure is the provision of between about 0.1–2 grams of antibiotic ingredient per day per dairy cow.

Publications which describe ionophorous antibiotics include U.S. Pat. Nos. 3,839,557; 5,217,993; J. Anim. Sci. 58(No.6), 1461–1483, 1484–1498, 1518–1527 (1984); Appl. Environ. Microbiol., 55(1), 1(1989); J. Dairy Sci., 80, 921 (1997); and technical articles cited therein, incorporated by reference.

Ionophores are naturally occurring cyclic polyethers containing multiple furan and tetrahydropyran structures. Ionophores are anabolites produced by bacteria:

| Sonophore | Strains |
|---|---|
| monensin | *Streptomyces cinnamonensis* |
| nigercin | *Streptomyces hydroscopicus* |
| tetronesin | *Streptomyces longisporoflavus* |

An ionophore is utilized in its natural form, or in the form of a physiologically acceptable derivative such as a sodium salt of the natural product or an analog thereof.

Ionophores differ in cation selectivity in their effect on microbial fermentation and biohydrogenation by ruminal bacteria. Monensin and nigericin are monovalent antiporters with selective binding affinity for $Na^+$ and $K^+$. Tetronasin is a divalent antiporter that preferentially binds with $Ca^{2+}$ and $Mg^{2+}$.

A main effect of ionophore presence in a rumen is a lower molar percentage of acetate, and a higher molar percentage of propionate. An ionophore also decreases methane production in the rumen.

An ionophore inhibits the rate of biohydrogenation of an unsaturated fatty acid such as linoleic acid under ruminal conditions. Any biohydrogenation of linoleic acid that occurs, yields less stearic and more oleic acid. There is an increased total of C-18:2 conjugated acids, mainly because of a cis-9, trans-11 C-18:2 isomer. This higher ruminal survival rate of unsaturated fatty acids is reflected in the profile of bypass lipid in the digestive tract. Consequently, the nutritional quality of the milk product from a lactating ruminant is enhanced for human consumption.

It appears that an ionophore reduces methane production by inhibiting the growth of gram-positive bacteria that produce hydrogen, and this moderates the biohydrogenation in the rumen. Effectively, a dietary ionophore alters lipid metabolism in the rumen, thereby increasing the unsaturated fatty acids in ruminal microbes and in the abomasum digesta.

The use of a lipid derivative having rumen-bypass properties in a present invention feedstock has additional advantage with respect to biohydrogenation by ruminal bacteria. Unsaturated fatty acids require a free carboxyl group in order to undergo biohydrogenation. A present invention lipid derivative with rumen-bypass capability permits increased passage of unsaturated fatty acids out of the rumen into the digestive tract.

In another embodiment this invention provides a lipid supplement for enriching the nutritive value of ruminant feedstock, wherein the supplement is a blend of ingredients comprising (1) unsaturated fatty acid derivative having rumen-bypass properties; and (2) between about 0.5–20 weight percent of cyclic polyether ionophorous antibiotic.

The unsaturated fatty acid derivative in the supplement can comprise fatty acid calcium salt and/or fatty acid magnesium salt and/or fatty acid amide. The unsaturated fatty acid moiety can comprise oleic acid and/or linolenic acid.

The ionophoric antibiotic ingredient in the lipid supplement can comprise monensin and/or nigericin and/or tetronasin and/or a physiologically acceptable derivative thereof.

In a further embodiment this invention provides a method of improving the lactational performance of ruminants, which consists of feeding a lactating ruminant with a feedstock comprising (1) a nutritionally balanced basal ration; (2) between about 2–20 weight percent, on a dry weight basis, of a lipid ingredient comprising unsaturated fatty acid derivative having rumen-bypass properties; and (3) between about 5–80 milligrams of cyclic polyether ionophorous antibiotic ingredient, on a dry weight basis, per kilogram of feedstock.

In a feeding regimen for lactating dairy cattle, it is preferred that the lipid ingredient in a feedstock comprises at least about 40 molar percent of unsaturated 18-carbon fatty acid constituents, so that the recovered milk product has increased nutritive and health values for human consumption.

Recent research also has shown that there are numerous components of milk fat that are potential anticarcinogenic agents [J. Nutr., 127, 1055 (1997)]. These include CLA, sphingomeyelin, butyric acid, and ether lipids. CLA is of the greatest interest. This CLA isomer of linoleic acid, formed mainly as a product of the ruminal biohydrogenation process, is the most potent natural anticarcinogen in foods [Cancer (Suppl.), 74, 1050 (1984)]. CLA occurs in milk fat in a quantity of about 0.3–0.8% of the total milk fat.

In addition to its anticarcinogenic effects, CLA has been reported to influence body composition (less fat, more muscle), improve bone growth, and stimulate immune function.

It is also known that increasing the consumption of omega-3 unsaturated fatty acids has human health benefits, particularly with alpha-linolenic acid, eicosapentaenoic acid (EPA) and docosahexaenoic acid (DHA). Omega-3 unsaturated fatty acids have been shown to reduce hypertension, and to lower serum lipids [Atherosclerosis, 62, 259 (1986)]. Omega-3 unsaturated fatty acids also are recognized as important dietary compounds for preventing coronary heart disease and alleviating inflammatory conditions, and for retarding the growth of tumor cells.

The following Example is further illustrative of the present invention. The components and specific ingredients are presented as being typical, and various modifications can be derived in view of the foregoing disclosure within the scope of the invention.

EXAMPLE

This Example illustrates the beneficial effects obtained by the feeding of ruminants with a feedstock formulated in accordance with the present invention.

A. Dairy Cattle

Eight Holstein cows are selected and equipped with rumen and duodenal cannulae. All cows are housed in individual tie stalls and are commencing the trial at 45 days in lactation.

The eight cows are employed in two four-by-four Latin Square designs. Each square has four cows with four treatments imposed. The four treatments are 0, 10, 40 and 70 mg/kg DM of dietary monensin. Each square has a different source of dietary fatty acids. In the first square, dietary fat is supplied by linseed oil, which has a high proportion of fatty acid linolenate. The second square has the dietary fat supplied by MEGALAC, which is a calcium salt of palm oil fatty acids having a high proportion of fatty acid oleate.

Cows are fed identical diets in both squares except for source of fatty acids, and are formulated for high production. Nutrient composition is formulated for all diets at 17% crude protein with 65% as rumen undegradable protein, 26% Neutral Detergent Fiber, 1.7 Mcal/kg net energy. All diets contain 4% added fat on a dry matter basis from MEGALAC or linseed oil. A daily dry matter intake of 25 kg/cow is calculated to deliver approximately 1 kg of linseed oil or MEGALAC per cow per day. Remaining dietary ingredients are low in fat, and include alfalfa haylage, corn silage, corn, barley, soybean meal, blood meal, Smartamine-M (rumen bypass methionine), sodium bicarbonate and vitamin-mineral premix. All diets are offered as Total Mixed Rations twice daily in quantities to assure at least 10% refusal per day of the amount offered.

Cows are fed their assigned diets for two weeks, with week one as an adaptation and week two as the experimental feeding period. Sampling is on the last 3 days of this second week. All cows are then moved onto a different diet in such a manner that by the end of the trial all cows have received all diets within each Latin Square.

During the second week of each period daily, dry matter intake and milk production are recorded. Total mixed rations are sampled daily and composited weekly. These are analyzed for crude protein, NDF and total fat. During the last 3 days of the second week individual proportional milk samples are taken and separated into two subsamples. One subsample is used to assay for total fat content and true protein, and the second is frozen for subsequent analysis of fatty acid profile in the milk.

During the last 3 days of the second week, rate of passage from the rumen is estimated using dye marker techniques. The liquid and solids markers are placed into the rumen daily beginning on day 7 of the adaptation period, with duodonal samples taken on the last 3 days of the experimental period. Duodenal samples are stored frozen for later analysis of total fat, fatty acid profile and marker. Concurrent rumen samples are taken. Liquid turnover rate is estimated from the dilution of dye in the liquid portion of rumen samples. Rumen contents are assayed for total fat, fatty acid profile and marker. Each Latin square is analyzed separately.

Results

Effect of Monensin in the Linseed Oil Diets

Monensin has no effect on DMI from 0 to 70 mg monensin addition. Milk production tends (P<0.1) to be improved by 3 lbs. per day at 10 mg monensin, and is improved (P<0.05) by 3.5 lb/day at 40 mg monensin with no further improvement at 70 mg monensin. Milk fat percentage is reduced (P<0.05) by 0.3 percentage points at 70 mg monensin, with only a tendency for a reduction at lower inclusion rates of monensin. Milk protein percentages are not different between cows fed the diets with different concentrations of monensin.

Rumen liquid turnover rate is not different between 0, 10 and 40 mg monensin but is increased (P<0.1) by 5% at the 70 mg level. Rumen rate of passage tends to increase (P<0.1) at the 10 mg level, and is increased by 6% at the 40 and 70 mg monensin inclusion rate in the diet.

Comparison of fatty acid profile of the diet vs. duodenal content indicates that at 10 and 40 mg monensin the amount of linolenic acid is increased (P<0.05) by 20 percentage points in the duodenal contents. The 0 mg monensin diet had an estimated rumen bypass rate for linolenic acid of 8%, which increases to 28% at the 10 and 40 mg monensin supplementation. At 70 mg monensin the bypass linolenic acid is about 30% which is not different (P<0.2) from the 10 and 40 mg level but is different (P<0.01) from the 0 mg monensin inclusion rate.

Milk fatty acid profiles reflects the altered rumen bypass of linolenate. Milk linolenate increased (P<0.05) by 25, 28 and 37% in cows supplemented with 10, 40 and 70 mg monensin in the diet, respectively, vs. the 0 mg supplementation.

Effect of Monensin in the MEGALAC Diet

Monensin has no effect on DMI from 0 to 70 mg monensin addition. Milk production tends (P<0.1) to be improved by 2.8 lbs. per day at 10 mg monensin, and is improved (P<0.05) by 3.9 lb/day at 40 mg monensin, with no further improvement at 70 mg monensin. Milk fat percentage is reduced (P<0.05) by 0.25 percentage points at 70 mg monensin, with only a tendency for a reduction at lower inclusion rates of monensin. Milk protein percentages are not different between cows fed the diets with different concentrations of monensin.

Rumen liquid turnover rate is not different between 0, 10 and 40 mg monensin, but is increased (P<0.1) by 6% at the 70 mg level. Rumen rate of passage tends to increase (P<0.1) at the 10 mg level, and is increased by 6.4% at the 40 and 70 mg monensin inclusion rate in the diet.

Comparison of fatty acid profile of the diet vs. duodenal content indicates that at 10 and 40 mg monensin the amount of oleic acid is increased (P<0.05) by 18 percentage points in the duodenal contents. The 0 mg monensin diet has an estimated rumen bypass rate for oleic acid of 56%, which increases to 74% at the 10 and 40 mg monensin supplementation. At 70 mg monensin the bypass linolenic acid is about 33%, which is not different (P<0.2) from the 10 and 40 mg level but is different (P<0.01) from the 0 mg monensin inclusion rate.

Milk fatty acid profiles reflects the altered rumen bypass of oleate. Milk oleate increased (P<0.05) by 22, 31 and 39% in cows supplemented with 10, 40 and 70 mg monensin in the diet, respectively, vs. the 0 mg supplementation.

B. Beef Cattle

Eight Hereford steers are selected and equipped with rumen and duodenal cannulae. All steers are housed in individual tie stalls. The duration of the trial is the last 90 days of the finishing period.

The eight steers are used in two four-by-four Latin Square designs. Each square has four steers with four treatments imposed. The four treatments are 0, 10, 40 and 70 mg of dietary monensin. Each square has a different source of dietary fatty acids. In the first square, dietary fat is supplied by linseed oil, which has a high proportion of fatty acid linolenate. The second square has the dietary fat supplied by MEGALAC, which is a calcium salt of palm oil fatty acids having a high proportion of fatty acid oleate.

Steers are fed identical diets in both squares except for source of fatty acids, and the diets are formulated for high rate of body weight gain (1 kg/day). All diets are calculated to deliver 0.75 kg/steer/day of added dietary linseed oil or MEGALAC. Remaining dietary ingredients are low in fat, and include corn silage, corn, barley, soybean meal, bloodmeal, Smartamine-M (rumen bypass methionine), sodium bicarbonate and vitamin-mineral premix. All diets are offered as Total Mixed Rations twice daily in quantities to assure at least 10% refusal per day of the amount offered.

Steers are fed their assigned diets for two weeks, with week one as an adaptation and week two as the experimental feeding period. Sampling is on the last 3 days of this second week. All steers are then moved onto a different diet in such a manner that by the end of the trial all steers have received all diets within each Latin Square.

During the second week of each period daily dry matter intakes are recorded. Total mixed rations are sampled daily and composited weekly. These are analyzed for crude protein, NDF and total fat. During the last 3 days of the second week individual body weights are recorded.

During the last 3 days of the second week rate of passage from the rumen is estimated using dye marker techniques. The liquid and solids markers are placed into the rumen daily beginning on day 7 of the adaptation period, with duodenal samples taken on the last 3 days of the experimental period. Duodenal samples are stored frozen for later analysis of total fat, fatty acid profile and marker. Concurrent rumen samples are taken. Liquid turnover rate is estimated from the dilution of dye in the liquid portion of rumen samples. Rumen contents are assayed for total fat, fatty acid profile and marker. Each Latin square is analyzed separately.

Results

Effect of Monensin in the Linseed Oil Diet

Monensin has decreased DMI. The 40 and 70 mg diets reduces DMI by 5%, with no significant effect at the 10 mg level. Rumen liquid turnover rate is not different between 0, 40 and 70 mg monensin, but is increased (P<0.1) by 5% at the 70 mg level. Rumen rate of passage tends to increase (P<0.1) at the 10 mg level, and is increased by 6% at the 40 and 70 mg monensin inclusion rate in the diet.

Comparison of fatty acid profile of the diet vs. duodenal content indicates that at 10 and 40 mg monensin the amount of linolenic acid is increased (P<0.05) by 24 percentage points in the duodenal contents. The 0 mg monensin diet has a rumen bypass rate for linolenic acid of about 10%, which increases to 34% at the 10 and 40 mg monensin supplementation. At 70 mg monensin the bypass linolenic acid is about 29%, which is not different (P<0.2) from the 10 and 40 mg level but is different (P<0.01) from the 0 mg monensin inclusion rate.

Effect of Monensin in the MEGALAC Diet

Monensin has no effect on DMI at 10 mg monensin addition. The inclusion of monensin at 40 and 70 mg reduces DMI by 8% compared to controls.

Rumen liquid turnover rate is not different between 0, 10 and 40 mg monensin, but is increased (P<0.1) by 4% at the 70 mg level. Rumen rate of passage tends to increase (P<0.1) at the 10 mg level, and is increased by 5.4% at the 40 and 70 mg monensin inclusion rate in the diet.

Comparison of fatty acid profile of the diet vs. duodenal content revealed that at 10 and 40 mg monensin the amount of oleic acid is increased (P<0.05) by 22 percentage points in the duodenal contents. The 0 mg monensin diet had an estimated rumen bypass rate for oleic acid of 66%, which increases to 88% at the 10 and 40 mg monensin supplementation. At 70 mg monensin the bypass linolenic acid is about 39%, which is not different (P<0.2) from the 10 and 40 mg level but is different (P<0.01) from the 0 mg monensin inclusion rate.

C. Lipid Supplement

Formulation of invention feedstocks are facilitated by the provision of nutrient supplements which comprise unsaturated fatty acid derivative having rumen-bypass properties, and about 0.5–20 weight percent of cyclic polyether ionophorous antibiotic.

Preferred lipid supplements include calcium salt and/or magnesium salt and/or amid derivatives of fatty acid mixtures obtained from converted oilseeds which include linseed, soybean, rapeseed, cottonseed, and safflower.

A suitable lipid supplement is composed of calcium oleate or oleamide, and 10 weight percent of monensin, nigericin or tetronasin.

D. Comparative Effects

1. Similar results are obtained when the antibiotic in the feedstock is monensin nigericin or tetronasin.

2. There is less biohydrogenation of unsaturated fatty acids in the rumen, and there is an increased passage of unsaturated fatty acids into the duodenal of the ruminant, with an invention feedstock.

3. There is increased production of propionate in the rumen, and a resultant improved feed efficiency and body growth in the ruminant with an invention feedstock.

4. Unsaturated fatty acid calcium salt and magnesium salt and amide derivatives in combination with an ionophorous antibiotic provide increased rumen-bypass of unsaturated fatty acids, in comparison with fatty acid glycerides or free fatty acids alone or in combination with an ionophorous antibiotic.

What is claimed is:

1. A supplemented feedstock adapted for beneficial feeding of a ruminant, which feedstock comprises (1) nutritionally balanced ration; (2) between about 2–20 weight percent, on a dry matter basis, of lipid ingredient comprising unsaturated fatty acid derivative having rumen-bypass properties; and (3) an effective quantity of cyclic polyether ionophorous antibiotic ingredient; wherein a ruminant feeding regimen with the feedstock induces an increased production of propionate in the rumen, and a resultant improved feed efficiency and body growth in the ruminant.

2. A feedstock in accordance with claim 1 wherein the fatty acid derivative comprises fatty acid alkaline earth metal salt.

3. A feedstock in accordance with claim 1 wherein the fatty acid derivative comprises fatty acid amide.

4. A feedstock in accordance with claim 1 wherein the quantity of ionophorous antibiotic, on a dry weight basis, is the range between about 5–80 milligrams per kilogram of feedstock.

5. A feedstock in accordance with claim 1 wherein the ionophorous antibiotic comprises monensin, or a physiologically acceptable derivative thereof.

6. A feedstock in accordance with claim 1 wherein the ionophorous antibiotic comprises nigericin, or a physiologically acceptable derivative thereof.

7. A feedstock in accordance with claim 1 wherein the ionophorous antibiotic comprises tetronasin, or a physiologically acceptable derivative thereof.

8. A feedstock in accordance with claim 1 wherein the feeding regimen is with a cow, sheep or goat.

9. A lipid supplement for enriching the nutritive value of ruminant feedstock, wherein the supplement is a blend of ingredients comprising (1) unsaturated fatty acid derivative having rumen-bypass properties; and (2) between about 0.5–20 weight percent of cyclic polyether ionophorous antibiotic.

10. A lipid supplement in accordance with claim 9, wherein the fatty acid derivative comprises fatty acid calcium salt and/or fatty acid magnesium salt and/or fatty acid amide.

11. A lipid supplement in accordance with claim 9 wherein the fatty acid derivative has a content comprising unsaturated fatty acid constituents which include oleic acid and/or linoleic acid and/or linolenic acid.

12. A lipid supplement in accordance with claim 9 wherein the ionophorous antibiotic comprises monensin and/or nigericin and/or tetronasin and/or a physiologically acceptable derivative thereof.

* * * * *